United States Patent [19]

Blümel et al.

[11] 4,279,514
[45] Jul. 21, 1981

[54] APPARATUS FOR THE ANALYSIS OF TEST TAPE

[75] Inventors: Reinhard Blümel; Jürgen Denker; Ernst Markart; Werner Trapp; Michael Tutzer; Reinhard Woznik, all of Munich, Fed. Rep. of Germany

[73] Assignee: Labora Mannheim GmbH für Labortechnik, Mannheim, Fed. Rep. of Germany

[21] Appl. No.: 3,857

[22] Filed: Jan. 16, 1979

[30] Foreign Application Priority Data

Jan. 30, 1978 [DE] Fed. Rep. of Germany ....... 2803849

[51] Int. Cl.³ ...................... G01N 21/55; G01N 21/00
[52] U.S. Cl. .................................. 356/445; 356/440; 356/244
[58] Field of Search ............... 356/445, 448, 440, 443, 356/416, 418, 419, 420, 244; 422/66

[56] References Cited

U.S. PATENT DOCUMENTS

| | | | |
|---|---|---|---|
| 3,910,701 | 10/1975 | Henderson et al. | 356/39 |
| 3,918,910 | 11/1975 | Soya et al. | 422/66 X |
| 4,047,820 | 9/1977 | Soodak et al. | 356/244 |

FOREIGN PATENT DOCUMENTS 2502013 9/1975 Fed. Rep. of Germany .

Primary Examiner—Vincent P. McGraw
Assistant Examiner—Rodney Bovernick

[57] ABSTRACT

Individual strips of test tape particularly suitable for urinalysis are held in longitudinal receptacles of a rotating drum and scanned by a measuring device operative to sense light reflecting characteristics of test areas on each test tape. The measuring device is moved along a guide mechanism longitudinally of the drum and the drum is indexed in steps to bring each test tape into sensing position relative to the measuring device. Analytical data from the measuring device may be converted into graphical form by a tracer mechanism operated in response to the measuring device. An endless belt driving mechanism operates to drive the measuring device longitudinally of the drum to scan the test tapes with a lever system containing a switch arm being provided to effect both reciprocal scanning motion of the measuring device and stepped rotation of the drum relative thereto.

36 Claims, 7 Drawing Figures

APPARATUS FOR THE ANALYSIS OF TEST TAPE

BACKGROUND OF THE INVENTION

The present invention relates generally to analysis apparatus and more particularly to a mechanism for performing analysis of test tape having discrete test areas arranged adjacent each other along the length of the tape. The invention is particularly directed toward apparatus especially suited for the performance of urinalysis of samples contained on the test tape. The apparatus of the invention is of the type which utilizes a reflex photometer to determine the reflection capability of test areas on the tape in order to derive analytical data.

Urinalysis tapes are used as an aid in medical diagnosis. Such tapes contain test areas which visibly discolor when they are brought into contact with certain substances contained in the urine. In such urinalysis, a discoloration which corresponds to a pathological concentration indicates a problem in an organ.

Each test tape contains several test areas which respond specifically to various substances in the urine. Since the chemical reactions in the test areas which cause discoloration to develop require the passage of a certain period of time, such discolorations develop only gradually. The developping coloring substances are frequently not stable and are altered under the influence of atmospheric oxygen or light. Therefore, the color and the depth of color of the test areas, which are a measure of the concentration of the substance to be analyzed, must be examined within a defined period of time after the test tape has been dipped into the urine sample. The evaluation of the concentration is frequently accomplished by a visual comparison utilizing color charts.

Since the human eye is not equally sensitive to all colors, the depth of color as a measure of the concentration of the substance is individually differently evaluated. By means of an analyzing apparatus for urinalysis tape known from German Offenlegungsschrift No. 25 57 872, it is possible to obtain analysis data which are independent of the individual conducting the analysis. This analyzing apparatus successively measures the reflection capability of individual test areas of a test tape by means of a reflex photometer. The reflex photometer has a measuring device with a light source which perpendicularly illuminates the test areas with monochromatic light and an integrating sphere or ball (Ulbricht's sphere) which receives the remitted light. In the integrating ball there is arranged adjacent the test area a photoelement for measuring light intensity in the integrating ball. The test tape to be analyzed lies in a receiving trough of a transport carriage which is moved by means of a drive motor in a longitudinal direction of the test tape beneath and past the measuring device of the reflex photometer.

To ensure clear results, the reflection capability must always be measured for a constant, predetermined period of time after the test tape has been dipped into the urine. To ensure this, the known analyzing apparatus contains a timer which is started at the time of dipping of the tape and which starts the movement of a carriage bearing the test tape only after a predetermined time period has elapsed. Since the carriage can only carry a single test tape, it is always necessary to await expiration of the entire predetermined time period before another test tape can be analyzed. The time period is usually in the order of magnitude of one minute. Accordingly, the known analyzing apparatus operates relatively slowly and is not particularly suited for performing a series of tests in which large amounts of test tapes must be analyzed.

The present invention is directed to the task of providing a simple analyzing apparatus for test tape, particularly urinalysis test tape, which can analyze the test tape automatically and which compared to known analyzing apparatus, can operate with increased analyzing frequency.

Another task to which the invention is directed is the provision of data in the form of measured values that can be documented. Moreover, the output data should be correlated to a scale related, for example, to normal or pathological concentrations. Furthermore, it is advantageous to design the apparatus in such a way that a clear correlation of sample and documented data can be carried out easily and without error.

SUMMARY OF THE INVENTION

Briefly, the present invention may be described as apparatus for the analysis of test tapes, particularly urinalysis tapes, comprising a cylindrical tape carrier or drum rotatably supported in a chassis and having therein a plurality of receptacles for receiving test tapes arranged parallel to the axis of rotation of the drum and angularly spaced apart in the circumferential direction of the drum. A measuring device movably guided in a guide member extending parallel to the axis of rotation is coupled, through a joint which can be disengaged perpendicularly to the direction of motion, to an endless traction member which is always driven in the same direction. The drum is in rotary engagement with a control gear, and a switch arm for effecting stepping operation of the control gear is coupled to the endless traction member.

In the operation of the analyzing apparatus of the invention the movements of the drum and of the measuring device are synchronized in a positive manner. A single motor which moves the endless traction member always in the same direction also effects reciprocal movement of the measuring device along the guide member and operates to shift the drum from one measuring position to the next.

The rate of rotation of the drum is selected such that the test tapes are turned from an inserting position to a measuring position during a predetermined time period which must elapse between dipping of the test tape into a urine sample and analysis of the sample. The frequency with which the successive test tapes are analyzed is independent from this time period and is defined merely by the number of receptacles provided on the drum between the inserting position and the measuring position. The axis of rotation of the drum is preferably arranged to extend horizontally, and the inserting position is selected to be at the top of the drum with the measuring position being selected to be at a side thereof.

After passing through the measuring position, the test tapes fall from their own weight from the bottom of the drum, and they may be received, for example, in a storage container arranged beneath the drum. Although the endless traction member may be intermittently driven, it is preferred to adjust the speed of the endless traction member in such a way that it is driven continuously and so that the transport of the drum is nevertheless effected in the predetermined time period. The endless traction member may be constructed as a chain, a belt or a toothed belt.

Two sections of the endless traction member which travel in opposite directions are guided so that there is provided a distance therebetween. The joint which couples the measuring device to the endless traction member compensates for changing distances of the endless traction member from the measuring device. The joint may, for example, be constructed as a pivot which is movably guided in a guide member and which is connected to the endless traction member. Structurally simpler embodiments may be provided wherein the joint coupling the measuring device to the endless traction member is constructed as a lever system which is connected with a spaced arrangement to the endless traction member and to the measuring device. Such an embodiment facilitates further structural simplification of the apparatus whereby the control gear is arranged adjacent a guide roller of the endless traction member and wherein the switch arm is supported by the lever system. The lever system and the switch arm are preferably constructed in one piece. The control gear may be arranged on a side of the guide roller which faces away from the endless traction member, with the switch arm gripping past the guide roller. In this manner, the actuating stroke of the switch arm can be made larger and may be better adjusted to the dimensions of the control gear.

The control gear can be connected directly to the drum. However, in the case of a drum with a large diameter, difficulties may arise particularly when, as is necessary in some embodiments, the control gear must project beyond the periphery of the drum. In this regard, preferred embodiments will have the control gear rotatably supported at the chassis about an axis which is parallel to the axis of rotation of the drum, with the control gear meshing with a gear wheel which is coaxially held at the drum. The path of engagement of the switch arm and the number of teeth of the control gear are preferably dimensioned in such a manner that the control gear can be stepped through an angular distance equivalent to at least two teeth for each switching movement of the switch arm. In this manner, relatively large switching angles of the control gear can be provided, with at least one tooth of the control gear continuously engaging a gear wheel mounted on the drum.

The receptacles for the test tapes formed in the drum are preferably constructed as troughs into which the test tapes are simply inserted. For holding the test tapes within the receptacles of the drum, a comb which is stationary relative to the chassis of the apparatus may be effectively utilized. Fingers of the comb extend in a circumferential direction between test areas of the test tapes about that part of the drum which faces toward the measuring device. In this manner, the test tapes are not only fixed during transport from the inserting position to the measuring position, but they are also firmly secured during actual measurement. The fingers need not elastically engage against the drum over its entire circumference, it being sufficient if they resiliently press the test tape into the receptacle in the measuring position.

A simpler structural embodiment of the comb may be obtained when the portion of the comb which holds the test tapes in the receptacles of the drum in the measuring position is formed by threads which are stretched tangentially closely around the drum perpendicular to its axis of rotation. The points where the threads are fastened can be slightly staggered relative to the axis of rotation of the drum, so that an elastic contact pressure will result from the inherent elasticity of the threads. Plastic threads are, for example, suitable for this purpose.

For guidance of the threads, circumferential grooves are preferably provided on the drum. Such circumferential grooves can also be formed by circumferential ribs arranged in spaced pairs on the drum. Since the threads as well as the drum will come into contact with the test tapes which have been dipped into the urine sample, the drum is formed together with a support for the threads as a structural unit which can be removed from the chassis for cleaning purposes.

In order to enhance the measuring accuracy of the analyzing apparatus, it is important that the measuring device be guided at a constant distance from the surface of the drum. For this purpose, the axis of rotation of the drum must extend exactly parallel to the guidance system of the measuring device. Even in the case of drums which can be removed from the chassis without complicated assembly and disassembly operations, parallelism can be achieved in a structurally simple manner in that, on axially opposite sides of the drum, there are provided circumferential guide surfaces engaged by guide rollers rotatably supported in the chassis which operate to secure the position of the drum relative to the measuring decive. Furthermore, contact rollers which resiliently rest against that side of the drum opposite the guide rollers are provided, and the axle of the drum is supported in support blocks which are open transversely to the axle. Accordingly, the drum merely rests on the support blocks and the correct distance of its axis of rotation from the measuring device is maintained by the guide rollers.

The reflection spectra of the test areas corresponding to the different substances in the urine generally differ from each other. More particularly, since the maximum reflections are at different wave lengths, the light source of the measuring device of the reflex photomoter should preferably emit monochromatic light having a light wave length which corresponds to the maximum of the reflection spectrum. For this purpose, suitable filters could be placed in front of the light source.

In a preferred embodiment of the measuring device, which may have importance independently from the analyzing apparatus described above, the measuring device is provided with a photoelement arranged aside the reflecting surface of the test area, with at least two focusing monochromatic light sources of different wave length being provided on either side of the photoelement to emit light rays directed obliquely to the reflecting surface at an angle such that its directly reflected light ray laterally passes the photoelement. Such a measuring device will have small dimensions and operate with sufficient accuracy even though it is capable of measuring at least two light wave lengths.

In the embodiment of the measuring device described above, the photoelement can be aligned perpendicularly to the reflecting surface. In this connection, it was found that the distance between the plane or flat light-absorbing surface of the photoelement and the reflecting surface of the test area can be made so small that the light-absorbing surface exhibits a sufficient integrating effect. Because of space requirements, the angles of incidence of the light from the light sources are preferably selected to be equal so that the light rays will impinge the reflecting surface at the base point of a perpendicular line extending from the photoelement to the reflecting surface. The reflection capability of test areas of the test tapes usually used in visual comparison with color scales can be best utilized, with respect to engineering of the measuring instruments, when one of the light sources emits red light and the other light source emits green light.

In order to enable utilization of the analyzing apparatus in as universal a manner as possible, it should be designed in such a way that test tapes with different amounts and combinations of test areas can be analyzed. If the reflex photometer of the apparatus has a measuring device which can be adjusted to different wave lengths, it should be possible to adjust the measuring device to the optimum wave length for each test area of the test tape. These requirements can be met in a structurally simple manner when the measuring device, which is slidable along its guidance system, carries the emitter and sensor of a photoelectric system or light barrier. Means are provided for selectively interrupting the light beam of the photoelectric system and such means may comprise a diaphragm which is a fixed part of the apparatus and an exchangeable control card.

The diaphragm and the control card will operate to control the driving arrangement and/or the reflex photometer by means of aligned, or at least partially overlapping, windows which control the light beam of the photoelectric system. One of two edges of the windows provided in the diaphragm is uniformly exposed and is arranged relative to the corresponding edge of a neighboring window in accordance with the spacing of the test areas of the test tape. The edges of the windows in the diaphragm which is a fixed part of the apparatus align the measuring device relative to the test areas of the test tape, the edges of the windows being arranged with the spacing of the test areas of the test tape. The exchangeable control card more or less covers the windows of the diaphragm and the extent of the coverage may contain additional information about whether or not the test tape contains a test area assigned to a window which is scanned at the moment and with what light wave length the test area is to be scanned. This embodiment of the control of an analyzing apparatus can also be utilized in other analyzing apparatus than the one described above.

It is of essential importance that in the output of data comprised of measurement results there is avoided transmission and conversion of errors. For this purpose utilization may be made of, for example, a suitable computer and a digital printer. In a preferred embodiment a curve tracer is utilized for recording the measurement results from the analyzing apparatus. Such a curve tracer may have utility in other analyzing apparatus and is characterized in that its stylus is held by a carriage which is movably guided along a guidance system transversely to the feed direction of a recording medium. The carriage has two drive surfaces which are parallel to each other and to the slide direction of the guidance system and which face toward each other. A drive wheel is engaged between the drive surfaces and is fixedly supported in the apparatus so as to be rotatable. The drive wheel is driven by a motor in the same direction and its diameter is smaller than the distance between the two drive surfaces. The guidance mechanism can be pivoted by means of an electromagnet about an axis which extends perpendicular to the plane through the two drive surfaces in such a manner that one or the other drive surface is alternatingly in drive connection with the drive wheel. By means of such a curve tracer there may be recorded on the recording medium, which may, for example, be a paper ribbon, peaks whose heights are proportional to the excitation period of the electromagnet. As long as the electromagnet is excited, the motor drives the carriage of the stylus in one direction through the drive wheel. When the electromagnet is switched off, a spring or, in the case of polarized electromagnets, an exciting signal of opposite polarity, couples the opposite drive surface with the drive wheel whereby the carriage is moved back into its initial position.

The advantage of this embodiment it that it is not necessary to change the polarity of the drive motor for the stylus and that, in addition, the structural design of the guidance system and of the drive mechanism of the stylus is relatively uncomplicated. By means of the curve tracer, when a conversion stage is connected to the input of the electromagnet, the value of a signal which is given numerically or as an amplitude can be recorded graphically in the form of a peak or tine whose length corresponds to the value. The conversion stage converts the value of the signal to be recorded into a control signal for the electromagnet, the duration of the control signal being proportional to the value of the signal to be recorded. Particularly suited for use as conversion stages are saw-tooth signal generators to which a comparator is connected which compares the saw-tooth signal with the value of the signal to be recorded.

The curve tracer may utilize a rack-and-pinion system as a suitable drive means or a frictional drive arrangement may be suitably provided.

It has been found advantageous to provide in the drive means which drives the carriage a recess which releases the drive connection to the drive wheel in a position of rest. In this embodiments, it is not necessary to switch off the drive motor between individual tracing steps.

The guidance system is advantageously constructed as a cylindrical rod having one end supported in an oversized bore of a flange which is rigidly connected to the apparatus and whose other end projects through between two adjustable stops which limit the angle of excursion of the rod. The oversize of the bore of the flange allows pivotal movement of the cylindrical rod which movements are limited by the stops independently from the maximum possible stroke of the electromagnet.

A significant simplification in the arrangement of the curve tracer may be obtained by providing a feed roller which is rigidly rotatably supported in the apparatus for feeding the recording medium. Through a reduction gearing, the feed roller may be rigidly connected to the drive wheel of the tracer carriage. The drive motor may thus be utilized not only for driving the stylus but also for feeding the recording medium.

Since the axes of the feed roller and of the drive wheel extend perpendicularly relative to each other, the reduction gearing may be advantageously constructed as a worm gearing whose worm is mounted on the shaft which also carries the drive wheel and whose worm wheel is mounted on an axle of the feed roller.

The curve tracer may be significantly improved by using a second feed roller arranged at a distance from the first feed roller and driven independently from this first feed roller. This is so because, by means of the second feed roller, the recording medium, for example, the recording paper, can be brought into a position relative to the first feed roller and that it is possible to inscribe characteristic data, for example, the name of the patient, on the recording medium during insertion of a test tape into the receptacle of the drum. Subsequently, the second feed roller conveys the recording medium into the intermediate space between the two feed rollers from where it can be pulled out when the corresponding test tape is in the measuring position. A separate writing surface can be provided which is arranged next to the feed rollers. If the feed rollers have a suitably smooth outer surface, the recording medium can be inscribed immediately on the feed rollers. To prevent the recording medium for slipping, the feed rollers are preferably constructed as spiked rollers.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described preferred embodiments of the invention.

DETAILED DESCRIPTION OF THE PREFERRED EMBODIMENTS

Figure 1:
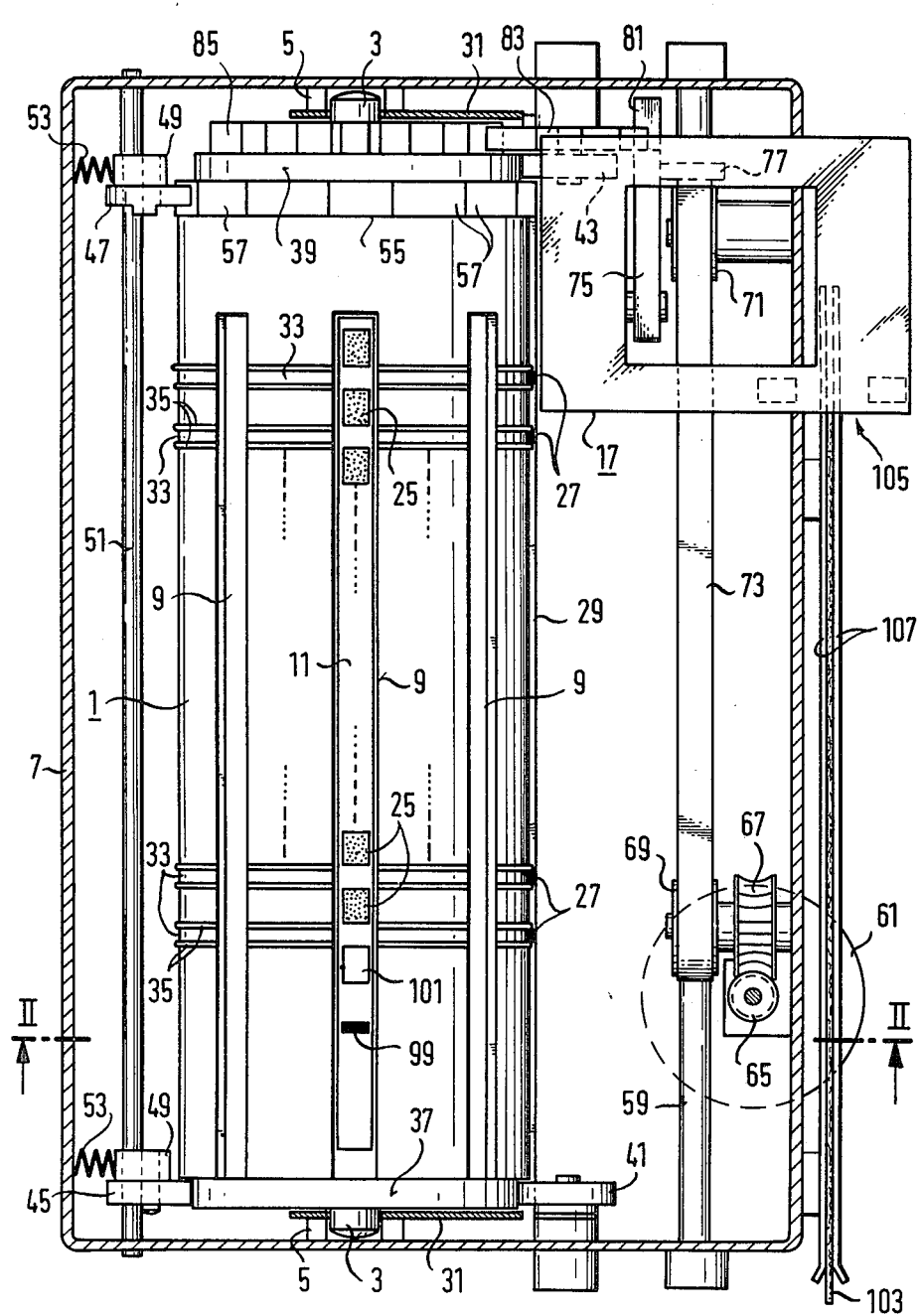
FIG. 1 is a sectional top view of apparatus for the analysis of urine test tape taken along the line I—I of FIG. 2.
Figure 2:
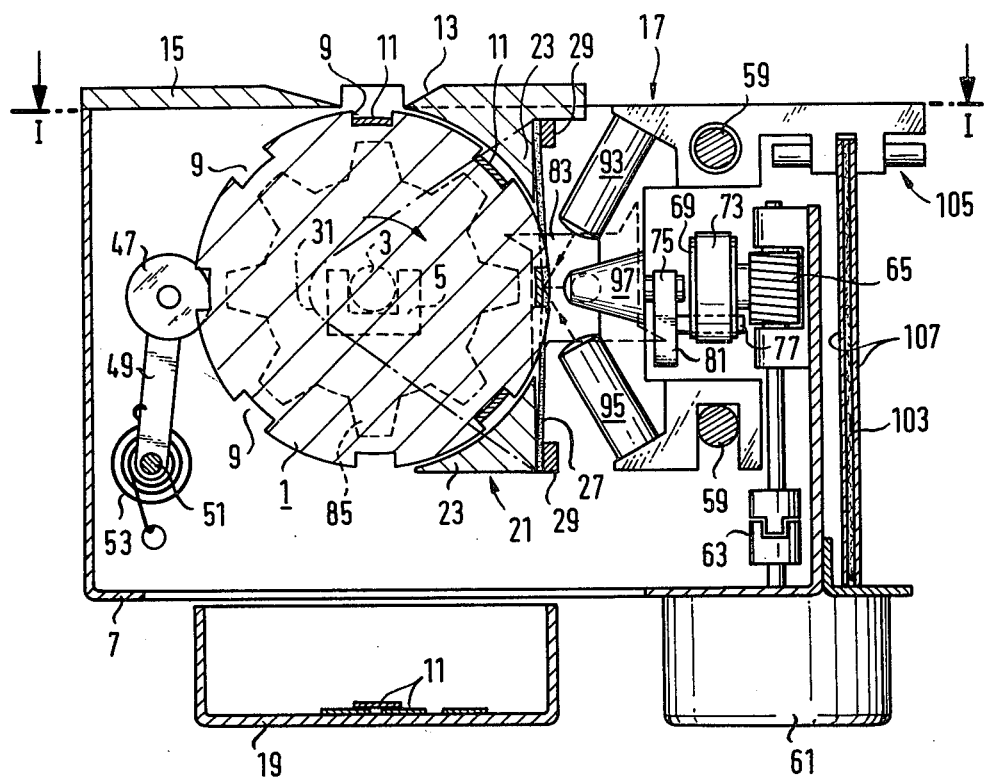
FIG. 2 is a sectional side view of the apparatus of FIG. 1 taken along the line II—II.

Referring to the drawings, wherein similar reference numerals are used to refer to similar parts throughout the various figures thereof, apparatus for automatically performing urinalysis with test tape is shown in FIGS. 1 and 2 as essentially comprising a cylindrical tape carrier or drum 1 having an axle 3 rotatably supported in a horizontal position in U-shaped support blocks 5 which are open upwardly and which are fastened to a chassis 7 of the apparatus. The drum or carrier 1 has a plurality of channels 9 serving as receptacles for urinalysis test tapes 11, with the receptacles or channels 9 being angularly spaced in the circumferential direction of the drum 1 and extending parallel to the axle 3.

Figure 3:
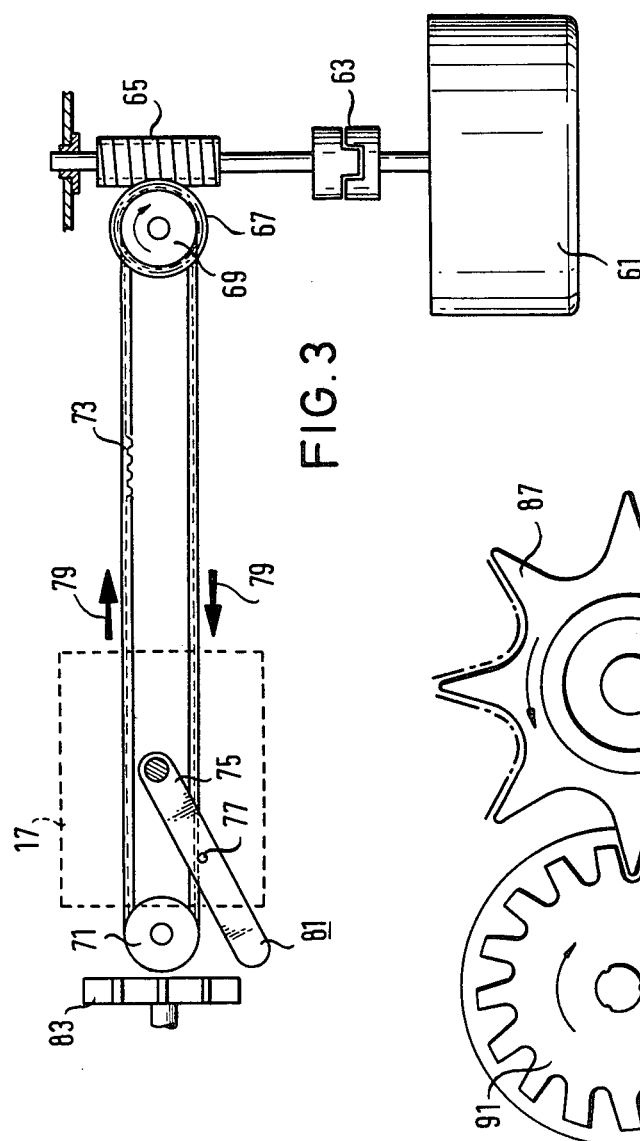
FIG. 3 is a schematic representation of a driving arrangement used in the apparatus according to FIGS. 1 and 2.

The drum 1 is rotated in a stepwise manner by means of a driving arrangement whose structure and operation may be best understood by reference to FIG. 3. The drum 1 is rotated in such a way that urinalysis test tapes 11 may be inserted at an inserting position defined on the upper side of the apparatus by a cutout 13 in a removable cover 15. The inserted tapes may then be transported within a predetermined time period into a measuring position shifted by 90° from the inserting position and in which the test tapes are located opposite a measuring device 17 comprising a reflex photometer, which is not illustrated in detail.

The urinalysis test tapes 11 which during the course of further rotation of the drum 1 are conveyed from the top side to the bottom side of the drum fall out of the receptacles 9 and are collected in a storage tray 19. To prevent the test tapes 11 from falling out early and to hold them securely against the bottom of the receptacle 9 in the measuring position, there is provided a multi-part comb 21 comprising lamellar fingers 23 which extend circumferentially on both sides of the measuring position. Fingers 23, in a manner not shown in detail, engage between the test areas 25 of the individual test tapes 11, the test areas 25 being arranged adjacent each other with a spacing therebetween in the direction of the axle 3. Moreover, the comb comprises elastic plastic threads 27 which are stretched tangentially relative to the surface of the drum 1 and which extend circumferentially thereof between ledges 29 of a support 31 which is held on the axle 3 and is shown in FIG. 2 in dash-dot lines.

As FIG. 1 shows, the threads 27 are guided in circumferential grooves 33 of the roller 1 between the test areas 25. The circumferential grooves are bordered axially on both sides by ribs 35 and reach to the bottom of the receptacles 9, so that, due to the inherent elasticity of the threads 27 which are slightly staggered toward the axle 3 the test tapes 11 are held in the receptacles 9.

Provided on the outer surface of the drum 1 are circumferential guide surfaces 37, 39 which are engaged on guide rollers 41, 43 rotatably supported in the chassis 7. Located approximately diametrically opposite the guide rollers 41, 43 are contact rollers 45, 47 rotatably arranged on arms 49. The arms 49 are pivotably mounted on a joint axle 51 which is supported in the chassis 7 and they are pretensioned in a direction toward the drum 1 by means of a pair of springs 53 each acting between the arm 49 and the chassis 7. As a result, the contact rollers 45, 47 press the drum 1 against the guide rollers 41, 43.

The contact roller 45 rests against the guide surface 37 of the guide roller 41, and the contact roller 47 rests against a notched track having indexing recesses 57 which are distributed over the circumference of the drum 1 in registry with the receptacles 9. The contact roller 47 fixes the position of rotation of the drum 1 relative to the measuring position. Together with the support 31, the drum 1 can be removed from the apparatus and, for example, it can be cleaned without problems after the cover 15 has been removed. After insertion of the drum 1, the guide rollers 41, 43 and the contact rollers 45, 47 automatically guide the drum into the correct position relative to the measuring device 17.

The measuring device 17 is slidably guided in guides 59 which run parallel to the axle 3 of the drum 1. An electromotor 61 drives a worm 65 of a worm gearing through a claw coupling 63. The worm wheel 67 of the worm gearing is rigidly coupled to a deflection wheel 69 of an endless toothed belt 73 which is guided parallel to the guides 59 by means of another deflection wheel 71. The measuring device 17 is coupled in an articulated manner to the endless toothed belt 73 through a lever system 75. In this case, the lever system 75 is hinged to a transverse pin 77 which is fastened on the outside of the endless toothed belt 73. The movement of the endless toothed belt 73, as indicated in FIG. 3 by arrows 79, is converted into reciprocal movement of the measuring device 17 along the guides 59 by means of the lever system 75.

The lever system 75 is arranged laterally relative to the endless toothed belt 73 and has extended therefrom a switch arm 81 which performs an upwardly directed switching movement when the transverse pin 77 is deflected by the deflection wheel 71. During this switching movement, the switch arm 81 engages a control gear 83 which is rotatably supported on the chassis about an axis extending transversely to the axis of rotation of the deflection wheel 71. The control gear 83 meshes with a gear wheel 85 which is mounted coaxially and rigidly on the drum 1. The switch arm 81, the control gear 83 and the gear wheel 85 are dimensioned in such a way that the drum 1 is rotated by an angular distance equivalent to two receptacles 9 during each switching stroke of the switch arm 81. The motor 61 can be operated continuously when the rate of rotation of the motor 61 and the step-down ratio of the worm gearing are selected such that the endless toothed belt 73 revolves a given number of times within each of the time periods prescribed for the test reaction of the urinalysis test tape and that the tape is conveyed from the inserting position into the measuring position.

Figure 4:
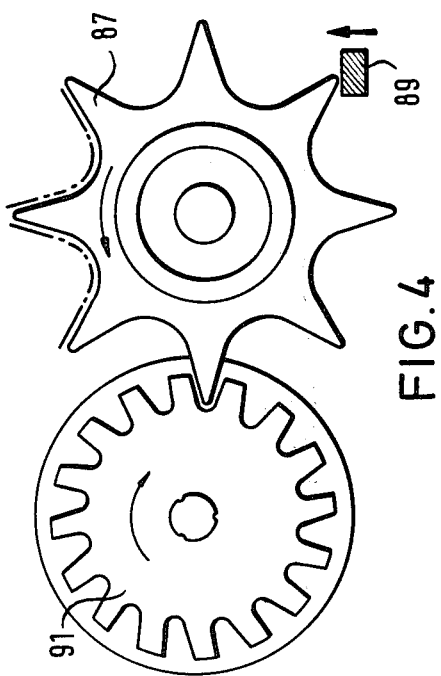
FIG. 4 is a schematic diagram showing a portion of the driving arrangement used in the apparatus according to FIGS. 1 and 2.

The control gear 83 shown in FIG. 2 is angularly stepped by one tooth spacing with each switching stroke of the switch arm 81. During stepping of the gear 83, one tooth always engages the gear wheel 85. FIG. 4 shows a control gear 87 which can be used instead of the control gear 83. The control gear 87 is actuated by a switch arm 89 which has the same function as the switch arm 81 and meshes with a gear wheel 91 which corresponds to the gear wheel 85. Compared to the gear wheels 83 and 85, the gear wheels 87 and 91 have twice the amount of teeth, wherein the control gear 87 and the switching stroke of the switch arm 89 are dimensioned in such a manner that the control gear 87 is always angularly turned through an angle equivalent to two teeth during each switching stroke. The embodiment according to FIG. 4 has the advantage of a more uniform transfer of force by the gear wheels 87 and 91.

Each urinalysis test tape contains several test areas 25, with each test area responding to different substances contained in the urine. The test areas 25 not only discolor in dependence on the concentration of the substance in the urine, but also in dependence of the reaction time. As a rule, the individual test areas of each test tape have different reflection spectra whose maximum values are at different wave lengths. The measurement of the reflection capability preferably takes place for the individual test areas at light wave lengths in the range of the maximum reflection. Therefore, the measuring device 17 contains two monochromatic light sources 93 and 95 which illuminate the center of the test areas which are in the measuring position with focused monochromatic light of different wave lengths. The angles of incidence of the light sources 93, 95 are equal, so that the directly reflected light ray of each light source is reflected toward the other light source.

Perpendicularly alongside the center of the test areas which are in measuring position there is arranged a photoelement 97 between the light sources 93, 95. The light sensitive surface of the photoelement 97 which faces toward the test area receives the light reflected from the surface of the test area and integrates the light to a certain extent on the basis of the size of the surface.

During operation, one of the light sources 93 or 95 is always switched on. This is accomplished in such a manner that for each test area there is switched on that light source whose light wave length is closer to the maximum of the reflection spectrum of the reaction color on the test area. The light sources can be constructed as light emiting diodes which can be operated in a pulsed mode for increasing the illuminating power. Preferably, one of the light sources is selected to emit green light, particularly with a wave length of 560 nm, while the other light source is selected to emit red light, particularly with a wave length of 635 nm.

The number of test areas on each urinalysis test tape may vary. To provide an indication of the beginning of a row of test areas on the test tape, each test tape is formed with a black strip 99 (FIG. 1), which generates a synchronizing signal to provide such an indication through the measuring device 17 in an electrical control device, not shown in detail. The synchronizing strip 99 is followed by a white test area 101 which does not react with the substances of the urine. The reflection capability of this test area 101 is measured by means of the measuring device 17 and is stored in the reflex photometer. The stored value of the reflection capability of the white test area 101 serves, in a manner known per se, as a comparison value in the subsequent measurement of the reflection capability of the test areas 25, wherein the stored value is utilized for the compensation of measurement errors; particularly, it is subtracted from the measured values. In this manner, for example, measurement errors which are caused by urine discoloration can be eliminated.

Control of the measuring device is effected by means of an exchangeable control card 103 which is assigned to the respective type of test tape and is inserted between two diaphragms 107 which are arranged in the light path of a photoelectric system of light barrier 105 mounted on the measuring device 17. The disphragms 107 as well as the control card 103 consist of an opaque material and have, as can be seen from FIG. 5, windows 109 which pass the light ray of the photoelectric system 105 at locations which overlap each other.

Figure 5:
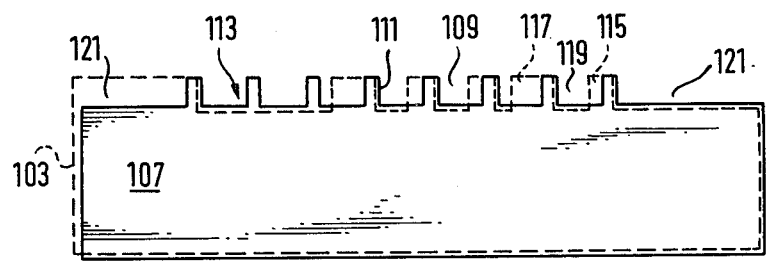
FIG. 5 is a schematic representation of a control card arrangement used for controlling the reflex photometer of the apparatus of FIGS. 1 and 2.

The windows of the diaphragms 107, which in FIG. 5 are illustrated in solid line, are arranged with a spacing corresponding to that of the test areas 25. The windows of the control card 103, shown in broken lines in FIG. 5, are formed in such a way that they uniformly do not shade one of the two edges extending in the longitudinal direction of the test tape—e.g., as illustrated in FIG. 5, the edge 111 on the left of the window of the diaphragm 107 - so that these edges 111 generate a synchronizing signal through the photoelectric system 105 indicating the position of the measuring device 17 relative to the test areas 25. The distance between the reference edge 111 of the diaphragm 107 and the edge of the control card 103 located oppositely in the window essentially comprises information which can be scanned by the photoelectric system 105. For example, the information may be coded in such a way that a completely open window of the diaphragm 107, as shown in FIG. 5 at 113, corresponds ot the lack of a test area, while the shading or blocking of that one-third of the window which is located opposite the reference edge 111, as for example in 115, indicates the presence of a test area. The one-third in the middle of each window may be utilized for the control of the monochromatic light sources 93 or 95 of the measuring device 17. For example, it may be provided that a shading 117 of the one-third in the middle of the window of the diaphragm 107 leads to a switching on of the light source 93, while the light source 95 is switched on when the one-third 119 in the middle of the window of the diaphragm 107 remains open. To be able to recognize whether the control card inserted between the diaphragms 107 is correctly assigned relative to the control strip 99, the diaphragms 107 contain windows 121 on both ends. However, a window corresponding to these windows 121 is only assigned on one side of the control card 103. The opposite window 121 of the diaphragm 107 is shaded by the control card 103.

For recording the measurement results for the individual test areas, a curve tracer is provided. This curve tracer writes graphs or tines 125 on an endless or continuous form or sheet 123, the length of the tine corresponding to a measured value. The endless form may be divided into individual sheets by means of transverse perforations (not shown) and the individual sheets each carry the tines for all test areas of a test tape including suitably imprinted scaling lines.

The curve tracer has a spiked roller 131 which engages the conveying holes 127 of the endless form 123 and is rotatably supported in a chassis 127 of the tracer. The spiked roller 131 moves the endless form 123 under a stylus 133 in the longitudinal direction of the form. The stylus is clamped into a chuck or holder 135 which, in turn, can be resiliently held in position and which is supported in a carriage 139 which slides along a guide bar 137. The guide bar 137 extends in a plane which is parallel to the axis of rotation of the spiked roller 131 and it is rotatably supported in an oversized bore of a flange 141 which projects from the chassis 129. Locking rings 143 secure the guide bar 137 against movement in the axial direction. A guide roller 144 which guides the carriage 139 on a side opposite the guide bar 137 prevents pivotal movement of the carriage 139 about the guide bar 137. The rotating movement of the guide bar 137 is limited by a double stop 145 which can be adjusted and fixed to all sides in the plane of rotation. An armature 147 of an electromagnet 149 located opposite the flange 141 operates, when excited, to pull the guide rod 137 from one stop phase of the double stop 145 to the opposite stop phase against the action of a pretensioning spring 151.

The carriage 139 has two racks 153, 155 which are arranged with a distance between each other and which face each other and extend parallel to the guide rod 137. Between the racks 153, 155 there engages a pinion 161 which is driven through a claw coupling 157 by a motor with a constant direction of rotation. The pinion 161 engages the rack 155 when the electromagnet 149 is not excited, and it engages the rack 153 when the electromagnet 149 is excited. Thus, the carriage 139 is reciprocally moved along the guide bar 137.

Figure 6:
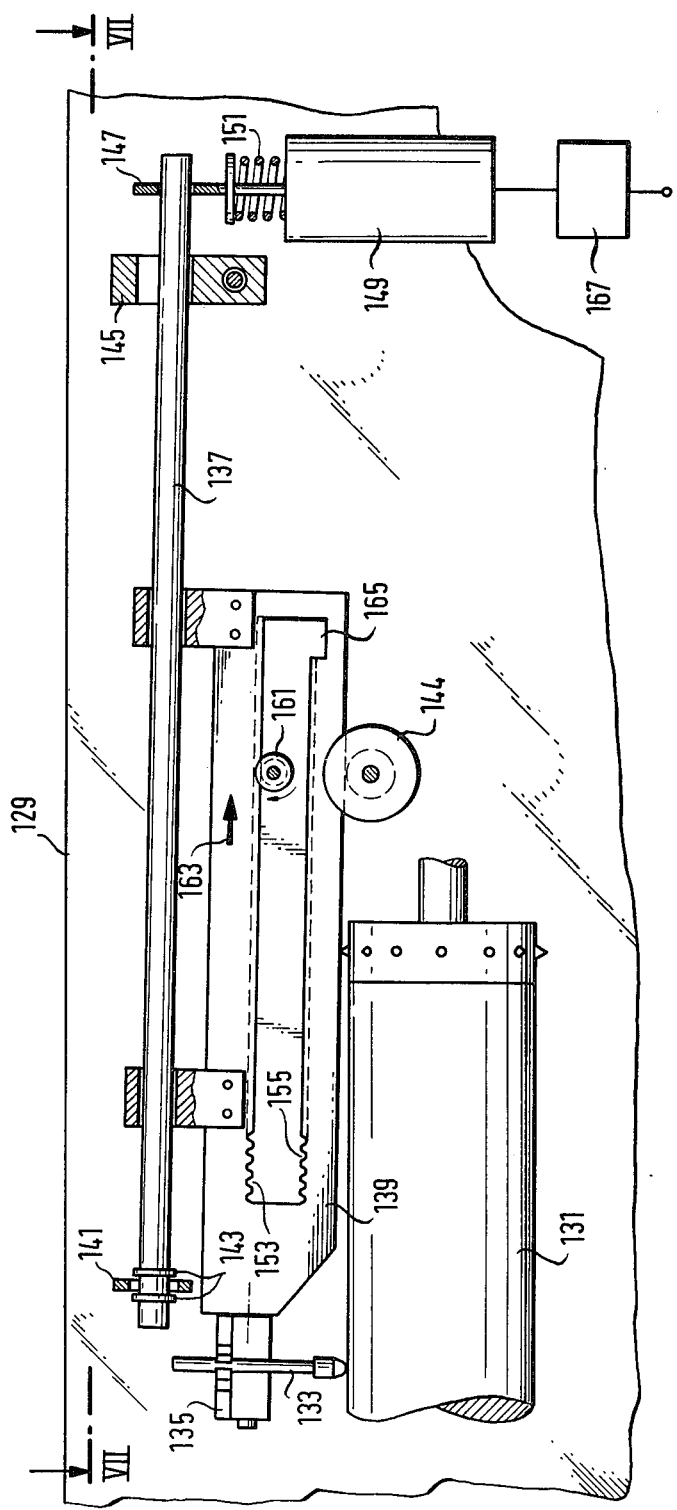
FIG. 6 is a partially broken away sectional view of a curve tracer taken along the line VI—VI of FIG. 7.
Figure 7:
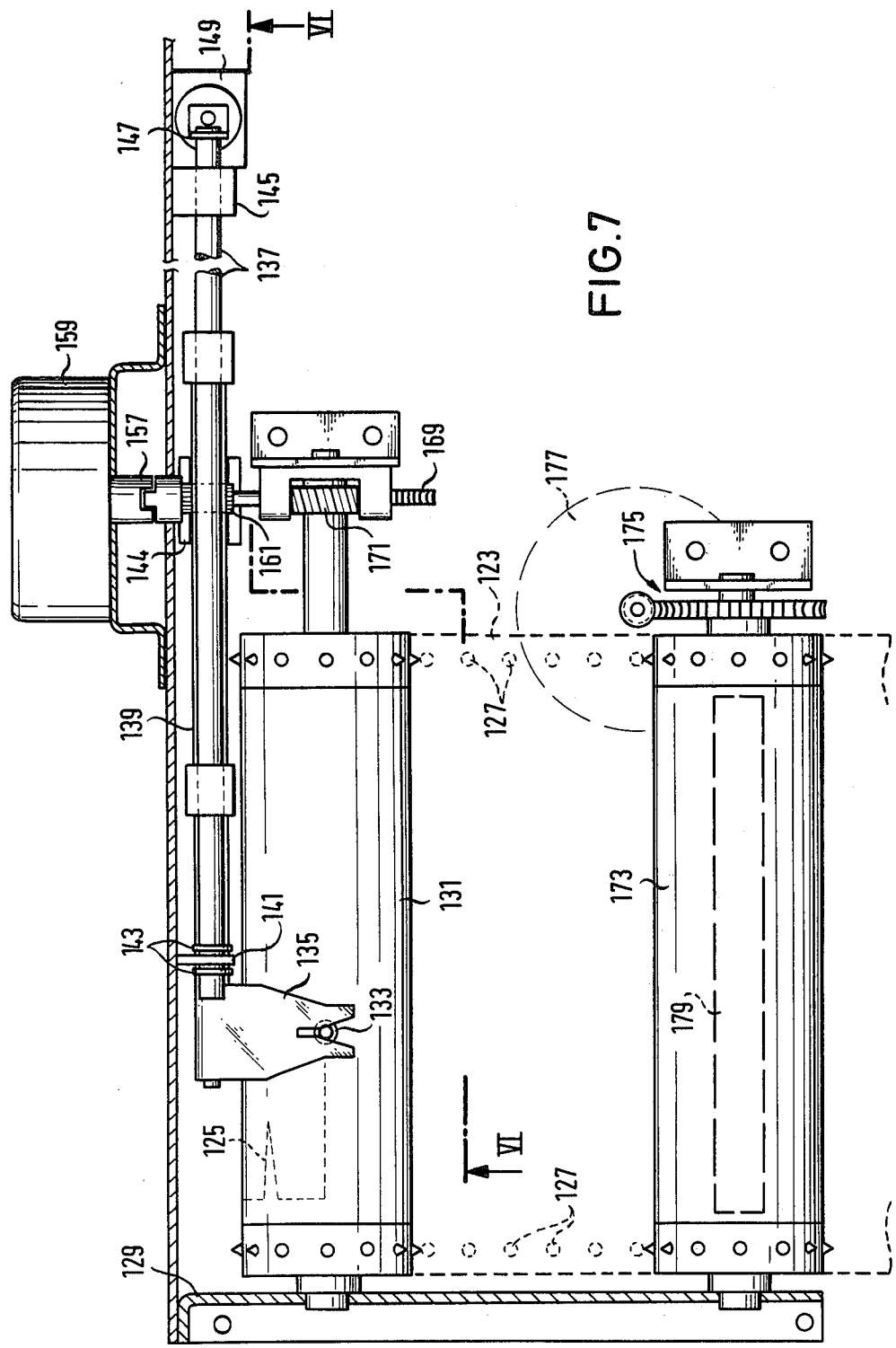
FIG. 7 is a top view of the curve tracer taken along the line VII—VII of FIG. 6.

For writing a tine similar to the tine 125, the electromagnet 149 is excited for a time period which corresponds to the measurement value to be written. As long as the electromagnet 149 is excited, the pinion 161 engages the rack 153 and drives the carriage 139 and thus the stylus 133, as indicated by an arrow 163 in FIG. 6, toward the right from the position of rest of the carriage. When the exciter signal of the electromagnet 149 is switched OFF, the pretensioning spring 151 swings the guide rod 137 upwardly and the pinion 161 meshes with the rack 155, the carriage 139 thereby being pushed back into the position of rest. In a position which corresponds to the position of rest of the carriage 139, the rack 155 has a recess 165 in which the pinion 161 can freely rotate. Accordingly, it is not necessary to switch OFF the motor 159 when the carriage 139 is in its position of rest.

If the reflex photometer emits signals whose voltage or current amplitude is proportional to the measured value, the electromagnet 149 must be followed by a converter 167 which converts the value of the signal to be recorded into an exciting signal for the electromagnet 149, its duration of excitation being proportional to the measured value to be recorded. The converter 167 may, for example, consist of a saw-tooth generator which is followed by comparator which compares the saw-tooth signals to the signal to be recorded and excites the electromagnet 149 so long as the saw-tooth signal is smaller than the signal to be recorded.

Since the pinion 161 can freely rotate in the recess 165 in the position of rest of the carriage 139, the electromotor 159 can also be utilized for driving the spiked roller 131. For this purpose, the shaft of the spiked roller 131 carries a worm gear 169 which meshes with a worm 171 which, together with the pinion 161, is mounted on a joint shaft which is driven by the motor 159.

For characterizing the individual sections of the endless form 123, for example, by writing the name of a patient thereon, before the corresponding urinalysis test tape is inserted, a second spiked roller 172 is provided which is arranged at a distance from the spiked roller 131 and is driven through a worm gearing 175 by an electromotor 177 independently from the spiked roller 131. The electromotor 177 is controlled by a control (not shown) of the analyzing apparatus in such a manner that an area 179, which is provided for an appropriate inscription on each section of the endless form 123, is always in writing position on the spiked roller 173 when the corresponding urinalysis test tape is being inserted into a receptacle of the drum 1 (FIG. 1) which is in the inserting position. Between the two spiked rollers 131 and 173, the endless form 123 forms a buffer loop so that the motor 177 can be turned off during the inscription of the area 179.

While specific embodiments of the invention have been shown and described in detail to illustrate the application of the inventive principles, it will be understood that the invention may be embodied otherwise without departing from such principles.

What is claimed is:

1. Apparatus for analyzing test tapes having test areas arranged adjacent each other therealong, particularly suited for urinalysis comprising: tape carrier means including at least one drum mounted for rotation about an axis; receptacle means defined on said drum for receiving and holding therein test tapes to be analyzed, said receptacle means comprising a plurality of longitudinal receptacles angularly spaced apart in the direction of rotation of said drum; measuring means for sensing said test areas of said test tape and for deriving therefrom analytical data, said measuring means including light source means and means for sensing light reflecting characteristics of said test areas; drive means for moving said measuring means longitudinally along said drum generally parallel to said axis to effect scanning of test tapes contained in said receptacles by said measuring means; guide means for effecting guided movement of said measuring means relative to said tape carrier means along said receptacles; and indexing means for effecting stepped rotation of said drum to individually bring test tapes contained in said receptacles into registry with said measuring means to enable scanning of said tapes by said measuring means; and indexing means including means in driven engagement with said drive means arranged to periodically effect said stepped rotation of said drum in accordance with a predetermined scanning cycle of said test tapes by said measuring means.

2. Apparatus according to claim 1 wherein said drive means comprise endless belt means driven in a constant direction of movement and joint means coupling said measuring means in driving engagement with said endless belt means to effect reciprocal movement of said measuring means.

3. Apparatus according to claim 2 wherein said indexing means comprise controlled gear means coupled in driving connection with said tape carrier means and switch arm means coupled with said endless belt means and engaging said controlled gear means to effect said stepped rotation of said drum.

4. Apparatus according to claim 3 wherein said joint means coupling said measuring means with said endless belt means is constructed as a lever system mounted in operative engagement between said endless belt means and said measuring means.

5. Apparatus according to claim 4 wherein said endless belt means comprise an endless traction member including a deflection roller and wherein said control gear means is arranged adjacent said deflection roller, with said switch arm means being fastened with said lever system.

6. Apparatus according to claim 5 wherein said control gear means is arranged on a side of said deflection roller facing away from said endless traction member and wherein said switch arm means extends past said deflection roller.

7. Apparatus according to claim 3 wherein said control gear means is mounted for rotation about an axis parallel to the axis of rotation of said drum and is arranged to operate in meshing engagement with a gear wheel arranged coaxially on said drum.

8. Apparatus according to claim 7 wherein said control gear means comprises a plurality of gear teeth arranged to be drivingly engaged by said switch arm means and wherein the path of engagement of said switch arm means and the number of teeth of said control gear means are dimensioned in such a manner that said control gear means is rotatively stepped through at least two of said teeth during each switching movement of said switch arm means.

9. Apparatus according to claim 1 further comprising comb means including finger elements thereof extending circumferentially of said drum between said drum and said measuring means, said finger elements being arranged to extend at locations between said test areas of said test tapes to support said test tapes within said receptacles of said drum.

10. Apparatus according to claim 9 wherein said finger elements of said comb means comprise portions which hold said test tapes in scanning position relative to said measuring means within said receptacles of said drum, said portions of said finger elements being formed as threads stretched tangentially about said drum perpendicularly relative to its axis of rotation.

11. Apparatus according to claim 10 wherein said drum is formed with circumferential grooves for guiding said threads.

12. Apparatus according to claim 9 wherein there is provided a support mounting said comb means together with said drum and wherein said drum and said comb means are formed as a single structural unit adapted to be replaceably removed from said apparatus.

13. Apparatus according to claim 1 further comprising axle means on said drum, support blocks having an open side for receiving therein in supporting engagement said axle means of said drum, guide surfaces defined at axially opposed ends of said drum and extending in a circumferential direction of said drum, rotatably mounted guide rollers engaging said guide surfaces, and contact rollers applied in resilient engagement against said drum on a side thereof opposite the side at which said guide rollers engage said guide surfaces, said drum being rotatably held in said support blocks and supported by said contact rollers at a fixed distance from said measuring means.

14. Apparatus according to claim 1 wherein said measuring means comprise a photoelectric element arranged to have said test areas of said test tapes located relative thereto as reflecting surfaces, and at least two focused monochromatic light sources of different light wave length arranged adjacent said photoelectric element, with the light rays of said light sources being directed to obliquely impinge said test areas at angles such that said test areas comprise reflecting surfaces which will directly reflect light laterally to said photoelectric element.

15. Apparatus according to claim 14 wherein said test areas are arranged to provide reflecting surfaces to reflect light to said photoelectric element, the direction of reception of said photoelectric element being aligned to be perpendicular relative to said reflecting surfaces.

16. Apparatus according to claim 14 wherein said light sources area arranged so that the angles of incidence of light emitted therefrom are equal.

17. Apparatus according to claim 14 wherein light rays from said light sources are directed to impinge said reflecting surfaces defined by said test areas of said test tape at the base point of a line perpendicular thereto directed from said photoelectric element onto said reflecting surfaces.

18. Apparatus according to claim 14 wherein said light sources and said photoelectric element are arranged relative to each other in such a manner that the light rays thereof extend within a single plane.

19. Apparatus according to claim 14 wherein one of said two light sources emits red light and wherein the other of said light sources emits green light.

20. Apparatus according to claim 1 further comprising photoelectric means including a light source and a light sensor spaced from said light source and adapted to sense a light beam emitted therefrom, said photoelectric means being mounted on said measuring means for movement therewith, and fixed diaphragm means adapted to receive therein exchangeable control card means, said diaphragm means and said control card means being arranged and configured to be located within the path of said light beam of said photoelectric means and to selectively interrupt said light beam as said photoelectric means is moved with said measuring means relative to said fixed diaphragm means, said photoelectric means being connected to control operation of said apparatus in accordance with the configuration of said fixed diaphragm means and said exchangeable control card means.

21. Apparatus according to claim 20 wherein said fixed diaphragm means and said exchangeable control card means define a plurality of windows through which said light beam of said photoelectric means may pass, said windows being located along the path of said photoelectric means and being configured to effect selective interruption of said light beam in accordance with a pattern of control to be effected by said photoelectric means of said apparatus.

22. Apparatus according to claim 21 wherein said diaphragm means is configured to define windows through which said light beam of said photoelectric means may pass, said windows of said diaphragm means having terminations thereof disposed in a pattern corresponding with the pattern of test areas on said test tape.

23. Apparatus according to claim 1 further comprising recording means for recording analytical data sensed by said measuring means, said recording means comprising a recording medium, means for feeding said recording medium in a given direction, stylus means for recording data on said recording medium, carriage means having said stylus means operatively mounted thereon, a guidance mechanism for moving said carriage means transversely to the feed direction of said recording medium, said carriage means being formed with a first and a second drive surface each facing toward each other and extending parallel relative to each other and parallel to the direction of movement of said guidance means, a drive wheel rotatably supported between said drive surfaces, means for rotatably driving said drive wheel, said drive wheel being formed with a diameter which is smaller than the distance between said first and second drive surfaces, and means including an electromagnet pivotally mounting said guidance means about an axis extending transversely to a plane through said first and second drive surfaces in such a manner that said drive surfaces may be alternately brought into driving engagement with said drive wheel as a result of said pivoting of said guidance means.

24. Apparatus according to claim 23 wherein said drive surfaces are constructed as racks and wherein said drive wheel is constructed as a pinion.

25. Apparatus according to claim 23 wherein said drive surfaces are constructed as friction surfaces and wherein said drive wheel is constructed as a friction wheel.

26. Apparatus according to claim 23 wherein one of said first and second drive surfaces is formed with a recess within which said drive wheel may move to release the drive connection of said drive wheel thereby providing a position of rest for said carriage means.

27. Apparatus according to claim 19 wherein said guidance mechanism is constructed as a cylindrical rod which is pivotally supported at one end within an oversized bore of a flange rigidly connected to said apparatus, with the other end of said rod extending between a pair of adjustable stops which limit the pivoting angle of said rod.

28. Apparatus according to claim 23 wherein said means for feeding said recording medium comprise a first feed roller rotatively mounted in said apparatus, said first feed roller being coupled with said drive wheel through a reduction gearing.

29. Apparatus according to claim 28 wherein said reduction gearing is constructed to include a worm gearing having a worm mounted on a shaft which also carries said drive wheel, and a worm wheel mounted on an axle of said first feed roller.

30. Apparatus according to claim 28 further comprising a second feed roller rotatably supported within said apparatus and spaced from said first feed roller, said second feed roller being arranged to be driven independently from said first feed roller.

31. Apparatus according to claim 30 wherein said first and said second feed rollers have said recording medium in operative engagement thereon and provide a smooth surface suitable for use as a writing surface for said recording medium.

32. Apparatus according to claim 30 wherein said first and said second feed rollers are constructed as spiked rollers.

33. Apparatus according to claim 23 further including converter stage means connected as an input to said electromagnet, said converter stage means operating to convert the value of a signal to be recorded by said recording means into a control signal for said electromagnet, the duration of said control signal being proportional to the value of a signal to be recorded.

34. Apparatus for analyzing test tapes having test areas arranged adjacent each other therealong, particularly suited for urinalysis, comprising: tape carrier means including at least one drum mounted for rotation about an axis; receptacle means defined on said drum for receiving and holding therein test tapes to be analyzed, said receptacle means comprising a plurality of longitudinal receptacles angularly spaced apart in the direction of rotation of said drum; measuring means for sensing said test areas of said test tapes and for deriving therefrom analytical data, said measuring means including light source means and means for sensing light reflecting characteristics of said test areas; drive means including an endless belt having said measuring means attached thereto for moving said measuring means and said tape carrier means relative to each other to effect scanning of test tapes contained in said receptacles by said measuring means; guide means for effecting guided movement of said measuring means relative to said tape carrier means along said receptacles; and indexing means for effecting stepped rotation of said drum to individually bring test tapes contained in said receptacles into registry with said measuring means to enable scanning of said tapes by said measuring means; said guide means including means extending parallel to said drum axis and engaging said measuring means to effect said guided movement thereof in directions parallel to said axis; said indexing means including gear means operatively engaging said drum and switch arm means on said endless belt, said switch arm means operating to periodically engage said gear means to effect said stepped rotation of said drum each time said measuring means is moved through a predetermined operating cycle by said endless belt.

35. Apparatus for analyzing test tapes having test areas arranged adjacent each other therealong, particularly suited for urinalysis, comprising: tape carrier means including at least one drum mounted for rotation about an axis; receptacle means defined on said drum for receiving and holding therein test tapes to be analyzed, said receptacle means comprising a plurality of longitudinal receptacles angularly spaced apart in the direction of rotation of said drum; measuring means for sensing said test areas of said test tapes and for deriving therefrom analytical data, said measuring means including light source means and means for sensing light reflecting characteristics of said test areas; drive means for moving said measuring means and said tape carrier means relative to each other to effect scanning of the test tapes contained in said receptacles by said measuring means; guide means for effecting guided movement of said measuring means relative to said tape carrier means along said receptacles; indexing means for effecting stepped rotation of said drum to individually bring test tapes contained in said receptacles into registry with said measuring means to enable scanning of said tapes by said measuring means; said indexing means including means in driven engagement with said drive means arranged to periodically effect said stepped rotation of said drum in accordance with a predetermined scanning cycle of said test tapes by said measuring means; and comb means including finger elements thereof extending circumferentially of said drum between said drum and said measuring means, said finger elements being arranged to extend at locations between said test areas of said test tapes to support said test tapes within said receptacles of said drum; said finger elements of said comb means comprising portions which hold said test tapes in scanning position relative to said measuring means within said receptacles of said drum, said portions of said finger elements being formed as threads stretched tangentially about said drum perpendicularly relative to its axis of rotation.

36. Apparatus for analyzing test tapes having test areas arranged adjacent each other therealong, particularly suited for urinalysis, comprising: tape carrier means including at least one drum mounted for rotation about an axis; receptacle means defined on said drum for receiving and holding therein test tapes to be analyzed, said receptacle means comprising a plurality of longitudinal receptacles angularly spaced apart in the direction of rotation of said drum; measuring means for sensing said test areas of said test tapes and for deriving therefrom analytical data, said measuring means including light source means and means for sensing light reflecting characteristics of said test areas; drive means including an endless belt having said measuring means attached thereto for moving said measuring means and said tape carrier means relative to each other to effect scanning of test tapes contained in said receptacles by said measuring means; guide means for effecting guided movement of said measuring means relative to said tape carrier means along said receptacles; indexing means for effecting stepped rotation of said drum to individually bring test tapes contained in said receptacles into registry with said measuring means to enable scanning of said tapes by said measuring means; said guide means including means extending parallel to said drum axis and engaging said measuring means to effect said guided movement thereof in directions parallel to said axis; said indexing means including gear means operatively engaging said drum and switch arm means on said endless belt, said switch arm means operating to periodically engage said gear means to effect said stepped rotation of said drum each time said measuring means is moved through a predetermined operating cycle by said endless belt; and comb means including finger elements thereof extending circumferentially of said drum between said drum and said measuring means, said finger elements being arranged to extend at locations between said test areas of said test tapes to support said test tapes within said receptacles of said drum; said finger elements of said comb means comprising portions which hold said test tapes in scanning position relative to said measuring means within said receptacles of said drum, said portions of said finger elements being formed as threads stretched tangentially about said drum perpendicularly relative to its axis of rotation.

* * * * *